United States Patent [19]

Volk

[11] Patent Number: 5,526,074
[45] Date of Patent: Jun. 11, 1996

[54] FULL FIELD REINVERTING INDIRECT CONTACT OPHTHALMOSCOPE

[76] Inventor: Donald A. Volk, 9378 Jackson St., Mentor, Ohio 44060

[21] Appl. No.: 332,404

[22] Filed: Oct. 31, 1994

[51] Int. Cl.[6] ............................................ A61B 3/00
[52] U.S. Cl. ............................................ 351/219; 351/205
[58] Field of Search ............................................ 351/219, 205

[56] References Cited

U.S. PATENT DOCUMENTS

| | | |
|---|---|---|
| 1,848,788 | 3/1932 | Loeck . |
| 4,248,506 | 2/1981 | Takahashi ............................... 351/6 |
| 4,367,018 | 1/1983 | Abe ............................... 351/205 |
| 4,666,268 | 5/1987 | Ito ............................... 351/206 |
| 4,679,921 | 7/1987 | Yamada ............................... 351/222 |
| 4,721,378 | 1/1988 | Volk ............................... 351/205 |
| 4,753,526 | 6/1988 | Koester ............................... 351/219 |
| 4,856,872 | 8/1989 | Spitznas et al. ............................... 350/255 |
| 4,934,809 | 6/1990 | Volk ............................... 351/205 |
| 4,964,717 | 10/1990 | Koester ............................... 351/219 |
| 5,009,487 | 4/1991 | Reiner ............................... 350/286 |
| 5,046,836 | 9/1991 | Volk ............................... 351/219 |
| 5,200,773 | 4/1993 | Volk ............................... 351/219 |
| 5,282,085 | 1/1994 | Volkert et al. ............................... 359/377 |
| 5,359,372 | 10/1994 | Kida et al. ............................... 351/219 |
| 5,430,506 | 7/1995 | Volk ............................... 351/205 |

*Primary Examiner*—William L. Sikes
*Assistant Examiner*—James A. Dudek
*Attorney, Agent, or Firm*—Spencer & Frank

[57] ABSTRACT

An indirect ophthalmoscopy lens system includes a contact lens device and a separate image erecting component. The contact lens device includes a first holder, a contact lens element having a concave posterior surface for placement on a cornea of a patient's eye and a first image forming lens system located anterior of the contact lens element and cooperating with the contact lens element for focussing light emanating from the retina of the patient's eye for forming a real, inverted, aerial image of the patient's retina anterior of the first image forming lens system. The first holder mounts the contact lens element and the first image forming lens system in a fixed relationship to one another. The image erecting component includes a second holder detached from the first holder and a second image forming lens system mounted within the second holder for receiving light rays forming the real inverted image anterior of the first image forming lens system for forming a real, re-inverted, aerial image of the patient's retina anterior of the second image forming lens system.

17 Claims, 4 Drawing Sheets

FULL FIELD REINVERTING INDIRECT CONTACT OPHTHALMOSCOPE

BACKGROUND OF THE INVENTION

The present invention relates to an indirect ophthalmoscopy contact lens system for observing and treating the retina of a patient's eye, and more particularly to an indirect ophthalmoscopy contact lens system which produces an erect, real, aerial image of the retina which can be viewed through a microscope for diagnostic, therapeutic and surgical purposes.

My prior U.S. Pat. No. 5,200,773 discloses an ophthalmoscopy contact lens system of this type which comprises a unitary device that is placed on a patient's eye for producing the erect, aerial image of the retina. This device includes a holder in which there is mounted a meniscus contact lens element having a concave posterior surface for placement on the cornea and an image forming lens mounted anterior to the contact lens element which collects light emanating from the retina and passing through the contact lens element to produce an inverted, real, aerial image of the retina anterior to the imaging forming lens. An erecting optical system is located inside the holder which reinverts the inverted image produced by the image forming lens to produce an erect, real, retinal image that can be viewed through a microscope, such as a slit lamp biomicroscope or operating microscope. The erecting system within the holder is disclosed in my prior patent as comprising a prism structure, such as a Pechan prism, or alternatively coaxial lenses anterior of the image forming lens which have refractive powers to enable a re-inversion of the inverted, aerial image.

One criteria of a unitary device such as that disclosed in my above mentioned patent is that the device have a relatively short length from the posterior surface of the contact lens element to the most anterior optical surface of the device so that the device can be positioned in a stable and comfortable manner on the patient's eye. If the device is too long, it can produce undesirable stresses on the patient's eye and is more subject to being inadvertently touched by the physician, for example, when maneuvering the microscope or surgical instrumentation. Through experimentation and development, I have found that a desirable length for the unitary device is less that 40 mm, and preferably closer to 30 mm. A unitary device containing a prism structure was made that met this length criteria. However, I have found that the prism structure renders a device that is too bulky in its width dimension and too heavy to be of practical use. Additionally the prism structure may limit the binocular field of view.

Non-contact, indirect ophthalmoscopy systems that produce an erect image are known which avoid the length criteria since, by design and use, they do not touch the eye. For example, David Volk discloses in his U.S. Pat. No. 4,721,378 a handheld, indirect ophthalmoscopy lens device of the non-contact type which produces an erect, aerial image of the retina that can be viewed through a microscope. The David Volk device includes three biconvex lenses mounted in a holder. In use, the lens that is closest to the patient's eye forms a real, inverted aerial image of the retina that is reinverted by the optics of the following two lenses. One difficulty associated with the use of this device is maintenance of optical alignment and positioning between the patient's eye and the viewing device such that the retinal image view is not diminished or lost during observation. Another drawback is that this non-contact device cannot achieve as large a field of view as a contact, indirect ophthalmoscopy lens.

U.S. Pat. No. 5,282,085 discloses a stereoscopic microscope in which a non-contact image forming lens together with inversion optics are provided as a removable attachment to the microscope. In the embodiment disclosed in FIG. 3 of this patent, the attachment comprises a three lens system similar to that of the above mentioned David Volk patent. A so-called field magnifying lens forms an inverted, aerial image of the patient's retina that is re-inverted by the following two lenses. In other embodiments of U.S. Pat. No. 5,282,085, the re-inversion is performed by a single lens or by a prism arrangement anterior of the field magnifying lens. In any case, the alignment between the inversion optics attachment, which includes the first image forming lens (i.e. the field magnifying lens), is fixed relative to the optical axis of the microscope. Although U.S. Pat. No. 5,282,085 offers some advantages with respect to the non-contact type ophthalmoscopy lens system with re-inversion optics, it still suffers from the fact that movement of the microscope together with the attachment relative to the patient's eye can easily result in diminution or loss of the fundus image, and the field of view is still limited relative to that of a contact indirect ophthalmoscopy lens system. Another disadvantage of this system relates to the proximity of the non-contact image forming lens to the patient's cornea which with a short focal length lens may be problematic.

SUMMARY OF THE INVENTION

It is an object of the invention to provide an indirect, contact ophthalmoscopy lens system with re-inversion optics to provide an erect, aerial image of the retina which is more easily maintained even with movement of the biomicroscope.

It is a further object of the invention to provide an indirect, contact ophthalmoscopy lens system with re-inversion optics to provide an erect, aerial image of the retina with a large field of view.

It is a further object of the invention to provide an indirect, contact ophthalmoscopy lens system wherein a stable, inverted, aerial image of the retina is formed by the image forming lens in such a manner that its various portions may be scanned through the microscope with the use of a separate image erecting component.

It is a further object of the invention to provide an indirect, contact ophthalmoscopy lens system with re-inversion optics separate from the contact lens system placed on the eye so as to minimize potential stress placed on the eye when used for diagnostic, therapeutic or surgical purposes.

The above and other objects are accomplished in accordance with the invention by the provision of an indirect ophthalmoscopy lens system, comprising: a contact lens device including a first holder, a contact lens element having a concave posterior surface for placement on a cornea of a patient's eye and a first image forming lens system located anterior of the contact lens element and cooperating with the contact lens element for focussing light emanating from the retina of the patient's eye for forming a real, inverted, aerial image of the patient's retina anterior of the first image forming lens system, the first holder mounting the contact lens element and the first image forming lens system in a fixed relationship to one another; and an image erecting component including a second holder detached from the first holder and a second image forming lens system mounted within the second holder for receiving light rays forming the real inverted image anterior of the first image forming lens system of the first holder for forming a real, re-inverted, aerial image of the patient's retina anterior of the second image forming lens system of the second holder.

According to one aspect of the invention there is further provided a means for mounting the image erecting component separate from and anterior to the contact lens device.

In one embodiment of the invention the image erecting component is mounted to a microscope through which the real, re-inverted, aerial image produced by the image erecting component can be observed. In one form of the invention, the image erecting component is mounted to the microscope so that the second image forming lens system has a fixed, coaxial relationship with an optical axis of the microscope. In other embodiments the image erecting component is mounted so that its position between the contact lens device and the microscope can be adjusted. For example, in one embodiment the image erecting component is mounted to be adjustably rotated about an optical axis of the microscope. In a further embodiment the image erecting component is mounted to be adjustably moved in a plane transverse to an optical axis of the microscope. In still another embodiment the image erecting component is mounted to be adjustably moved in a direction extending between the contact lens device positioned on the eye of a patient and the microscope. In yet a further embodiment the image erecting component is mounted to the microscope by way of one or more universal joints for universally pivoting the image erecting component.

According to another embodiment of the invention, the second image forming lens system comprises first and second lens systems spaced from one another and cooperating for forming the real, re-inverted, aerial image of the patient's retina anterior of the second lens system. Desirably, the second image forming lens system may further include optical means for minimizing a working distance from the microscope such as a telephoto lens system or a light folding means operatively arranged with the first and second lens systems. The light folding means may comprise a prism structure and/or mirrors.

The working distance required by the microscope may be further reduced according to another aspect of the invention by fixing a lens of positive optical power to the end of the microscope to reduce the effective focal length of the microscope.

In still another embodiment of the invention, one of the lens components of the second image forming lens system is mounted within the holder of the contact lens device. The remaining lens component or components which collect and focus the light to form the erect, aerial image are mounted in the separate holder of the image erecting component.

Further objects, features and advantages of the invention will become apparent from the following detailed description when read in conjunction with the accompanying drawings.

DETAILED DESCRIPTION OF THE PREFERRED EMBODIMENTS

Figure 1:
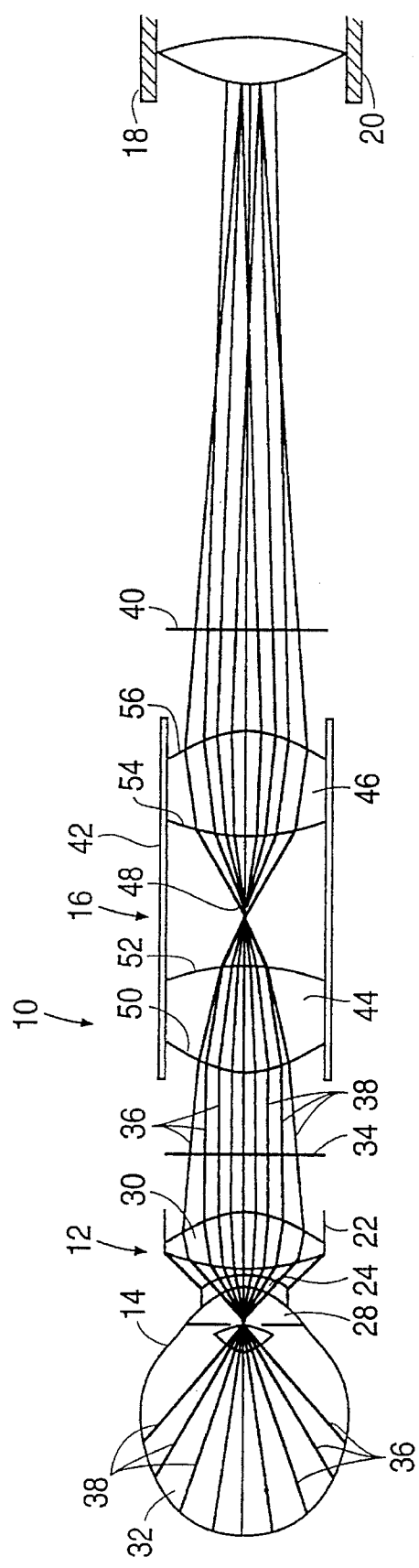
FIG. 1 is a schematic section of a lens system, including the path of principal rays, according to a first embodiment of the invention with the holder of the image erecting component detached from both the contact lens device and a viewing microscope.

Referring to FIG. 1, there is shown a schematic of a longitudinal section of an indirect ophthalmoscopy lens system 10 according to a first embodiment of the invention. Lens system 10 includes a contact lens device 12 positioned on an eye 14 of a patient and a separate image erecting component 16 positioned between contact lens device 12 and an objective lens 18 of a microscope 20, the end of which is only partially shown for purposes of this description.

Contact lens device 12 comprises a first holder 22 in which there is mounted a meniscus-type contact lens element 24 having a concave posterior surface 26 adapted for placement on the cornea 28 of the patient's eye 14. A bi-convex image forming lens 30 is mounted in holder 22 anterior of contact lens element 24 for collecting light rays emanating from the retina 32 of the patient's eye 14 and passing through contact lens element 24 for forming an aerial image 34. The lens prescriptions for contact lens element 24 and image forming lens 30 as well as the general construction of contact lens device 12 may be in accordance with my prior U.S. Pat. No. 5,200,773, the disclosure of which is incorporated herein by reference. The present invention is not limited to any particular indirect ophthalmoscopy contact lens device, as any commercially available indirect ophthalmoscopy contact lens device which produces an aerial image of the retina could be used in combination with the image erecting component 16 as explained below.

In an exemplary implementation, the power of the contact lens device 12, including contact lens element 24 and image forming lens 30 is about 150 Diopters. Contact lens element 12 is made of acrylic having an index of refraction of 1.491, has an apical posterior radius of 7.7 mm with a conic constant of −0.18, an apical anterior radius of 7.4 mm with a conic constant of −0.18, and a thickness of 2 mm. Image forming lens 30 is spaced from contact lens element 24 by 0.5 mm, is made of LAH58 glass having an index of refraction of 1.883, has a apical posterior radius of 17.66 mm with a conic constant of −3.5456, an apical anterior radius of 8.83 mm with a conic constant of −3.5456 and a thickness of 6 mm. The total length of contact lens device 12 from the posterior surface of contact lens element 24 to the anterior surface of the image forming lens 30 is thus 8.5 mm. As is well known, the retinal image produced by an indirect ophthalmoscopy lens device such as that illustrated in FIG.

1, is a real image of the retina which is inverted, as can be seen by following the chief rays 36 which emanate from a lower portion of the retina as viewed in FIG. 1 and are focused by contact lens device 12 at the upper region of image 34 whereas the chief rays 38 emanating from an upper region of the retina as viewed in FIG. 1 are focused by contact lens device 12 at a lower region of image 34.

In the embodiment of FIG. 1, image erecting component 16, in its most simple form, is a handheld device that can be manipulated by the physician looking through microscope 20 for scanning image 34 and creating a reinverted, i.e., erect, real image 40, of the patient's retina which can be viewed through microscope 20. Image erecting component 16 includes a second holder 42 which mounts a second image forming lens system and includes first and second lenses, 44 and 46, respectively. Lenses 44 and 46 may each be comprised of a plurality of lens elements, including achromatic lenses, as will be readily apparent to those skilled in the art. In the most simplified form of the invention, however, lenses 44 and 46 each comprise a single, high-powered lens on the order of 100 Diopters. First lens 44 converges light rays exiting from image forming lens 30 to re-image the patient's pupil where the chief rays cross one another at location 48, after which the light rays continue and are collected by second lens 46 for forming the erect, aerial image 40.

In one implementation of image erecting component 16, lenses 44 and 46 are made of SK16 glass having an index of refraction of 1.62. The posterior surface 50 of first lens 44 has an apical radius of 9.165 mm with a conic constant of −2.7, and the anterior surface 52 has an apical radius of 14.66 mm with a conic constant of −2.7, with the center thickness of the lens being 12 mm. The second lens 46 is spaced from first lens 44 by a distance of 13.5 mm and is constructed identically to first lens 44 except its orientation is reversed, with its posterior surface 54 having the larger apical radius and its anterior surface 56 having the smaller apical radius. Second holder 42 is suitably constructed of metal or plastic for holding first and second lenses 44 and 46 in a fixed relationship.

In operation, contact lens device 12 is placed on the cornea of a patient's eye. For vitrectomy surgery, contact lens device 12 may be adapted to fit into a vitrectomy ring which can be sutured directly to the scleral surface, for example, as disclosed in my aforementioned U.S. Pat. No. 5,200,773. Image erecting component 16 may then be positioned between the contact lens device 12 and the microscope either manually by the physician utilizing the microscope or his assistant, or with the aid of a lens positioning device, such as disclosed in my prior U.S. Pat. No. 4,934,809, the disclosure of which is incorporated herein by reference. The lens positioning device may be fixed to a surface of the viewing microscope or alternatively to another fixed surface such as a fixture connected to a surgical bed on which a patient is resting during a surgical procedure. The position of image erecting component 16 is adjusted in the direction extending between the microscope and contact lens device 12 to present a clearly focused, erect aerial image 40 of the patient's retina which is viewed through the microscope. In addition, image erecting component 16 can be moved in a direction transverse to the optical axis of the microscope for scanning the inverted image 34 to thus create an erect image of a selected portion of the patient's retina more centrally located in the visible field as seen through the microscope.

Figure 2:
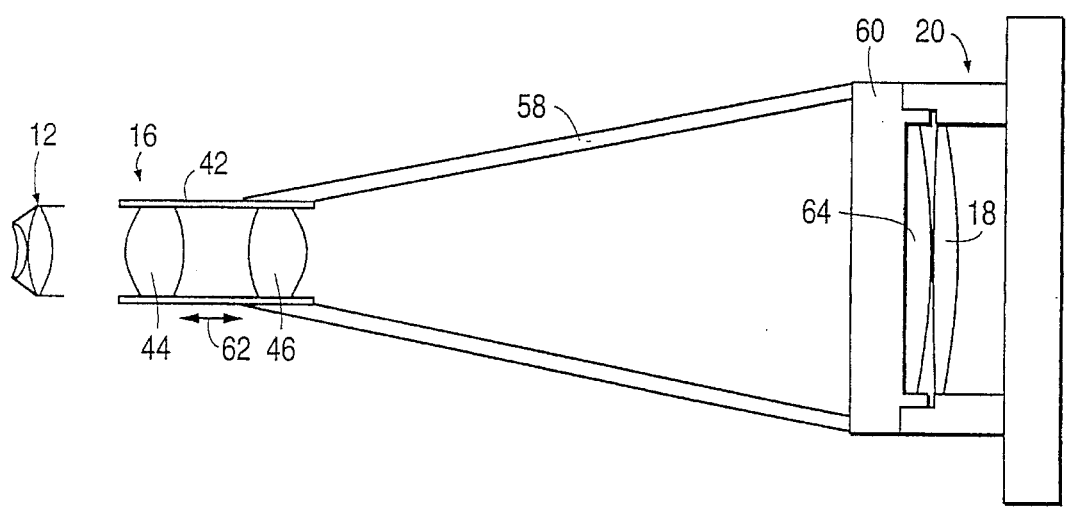
FIG. 2 is a schematic section illustrating another embodiment of the invention with the holder of the image erecting component fixedly mounted to the end of a microscope.

FIG. 2 shows another embodiment of the invention wherein holder 42 of image erecting component 16 is connected to the end of microscope 20 by a cone-shaped connecting element 58 which at its wider end is removably fixed to a connecting ring 60 which is adapted to fit on the end of microscope 20 by means of a bayonet mount or a screw mount, neither of which are illustrated in detail. Image erecting component 16 may be removably fixed to the narrow end of cone-shaped connecting element 58 or slidably mounted to connecting element 58 so that image erecting component 16 can be moved toward and away from contact lens device 12 as shown by arrow 62 for optimally positioning and focusing the erect aerial image produced anterior of image erecting component 16 without moving microscope 20. Desirably, a lens 64 having positive optical power, for example, approximately 2.5 Diopters or higher, is mounted on connecting ring 60, adjacent objective lens 18 of the microscope reducing the effective focal length of the microscope and thus reducing the required distance between the microscope and image 40.

Figure 3:
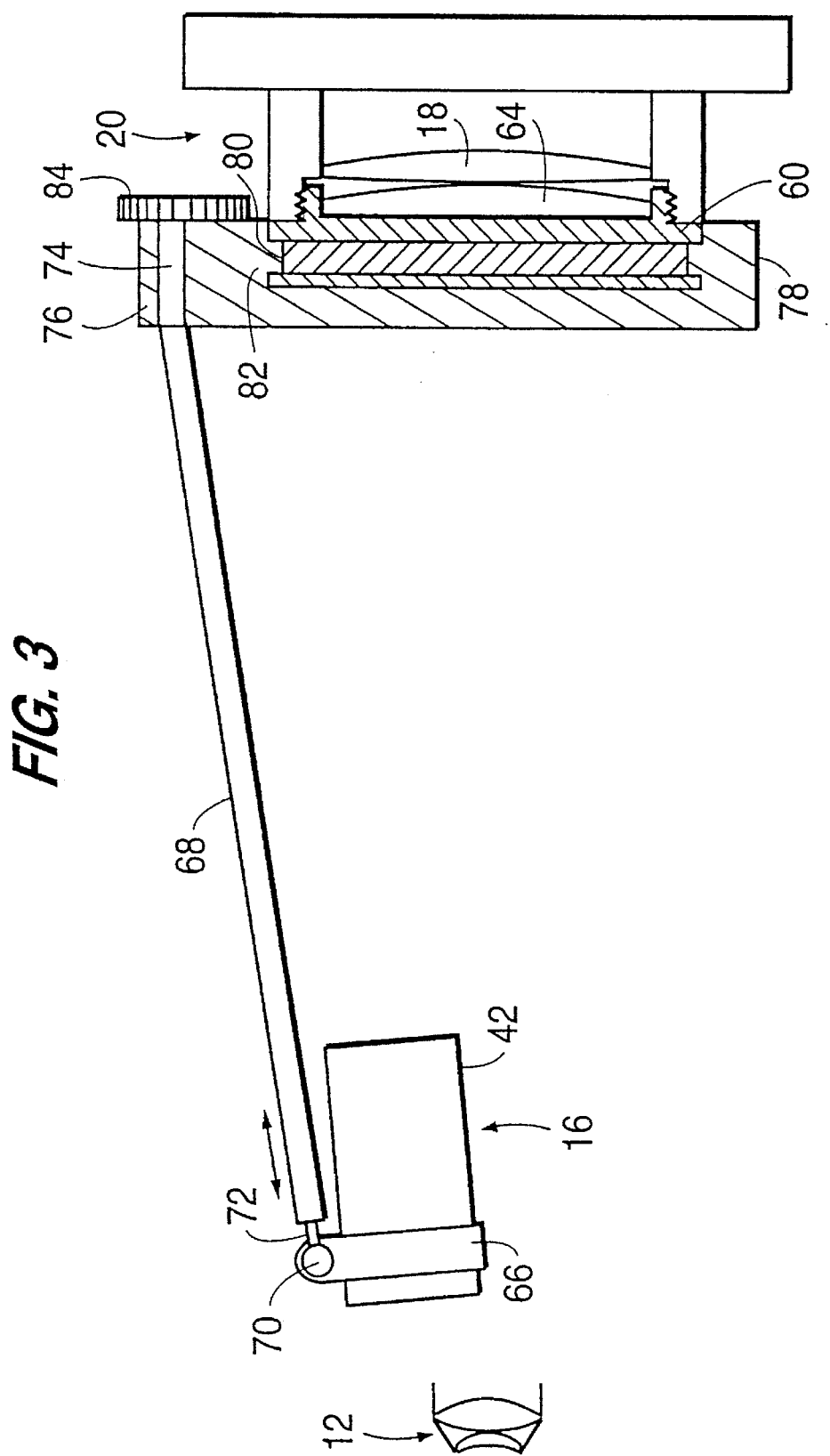
FIG. 3 is a schematic section illustrating a further embodiment of the invention with the holder of the image erecting component mounted to the end of a microscope by a mechanism that permits adjustment of the position of the image erecting component relative to the microscope and the contact lens device.

FIG. 3 illustrates a further embodiment of the invention which permits greater flexibility in positioning image erecting component 16 relative to contact lens device 12 and microscope 20. In this embodiment, holder 42 of image erecting component 16 is held by a clamp 66 which is connected to an arm 68 by way of a ball and socket arrangement 70 fixed to one an end of a telescoping arm 72 that slides within arm 68. The other end of arm 68 has an angled portion 74 which is rotatably mounted in a ring 78 which itself is rotatably coupled to a modified connecting ring 60' which mounts lens 64 to the end of microscope 20 as previously described. Ring 60' has a groove 80 for receiving a correspondingly shaped projection 82 of ring 78 in a manner that permits ring 78 to be adjustably rotated about the optical axis of microscope 20. Angled portion 74 of arm 68 is connected to a knurled knob 84 by which arm 68 can be rotated which will cause image erecting component 16 to traverse an arcuate path transverse to the optical axis of the microscope. Rotation of ring 78 relative to microscope 20 will cause image erecting component 16 to traverse a circular path about the visible microscope field in a plane transverse to the optical axis of the microscope. Alternatively, or in addition to the telescoping rod 72, lens 44 and 46 (not shown in FIG. 3) may be slidably mounted within holder 42 to provide a further adjustment of the second image forming lens system. The embodiment of FIG. 3 thus gives the doctor operating microscope 20 complete flexibility in adjusting the position of image erecting component 16 for forming a clearly focused, wide field, erect image of the retina and for allowing image erecting component 16 to scan the real inverted image created anterior of contact lens device 12 which remains essentially fixed in space.

Figure 4:
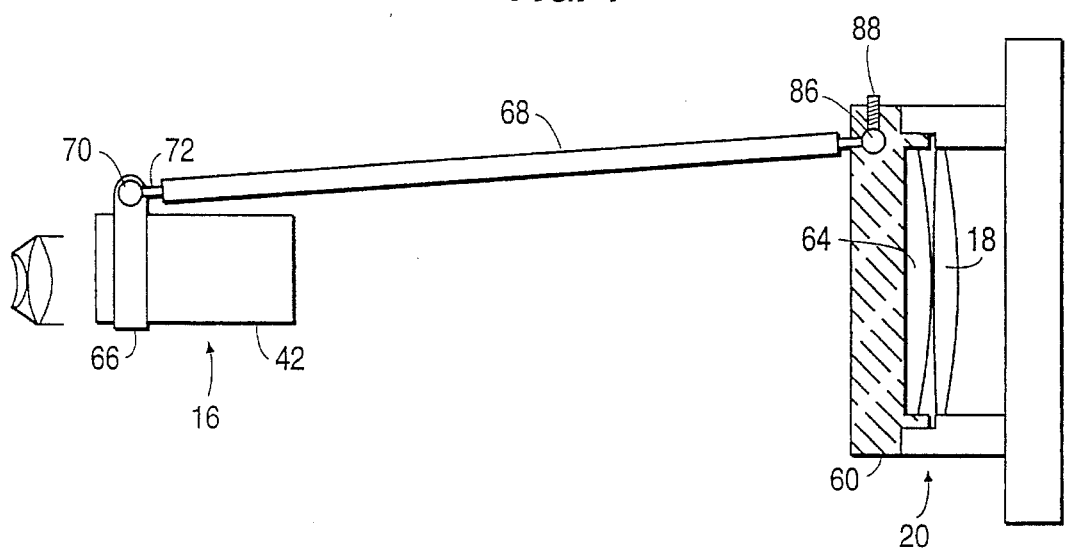
FIG. 4 is similar to FIG. 3 showing a modified mechanism for adjustably moving the image erecting component relative to the microscope and the contact lens device.

FIG. 4 shows a further embodiment of the invention which is similar to the embodiment illustrated in FIG. 3 except that the right hand end of rod 68 in FIG. 4 is connected by a ball and socket arrangement 86 to the ring 60 described and illustrated in connection with FIG. 2. Ball and socket arrangement 86 may facilitate placement of rod 68 in a desired angular position relative to microscope 20 which position can be maintained by way of a tension adjustment set screw 88 and possibly a compression spring (not shown) interposed between set screw 88 and the ball of ball and socket arrangement 86. The arrangement of FIG. 4 has the advantage of allowing the position of image erecting component 16 to be adjusted in essentially one step as opposed to the embodiment of FIG. 3 which requires adjustment of rod 68 by way of knurled knob 84 and a separate rotation of rotatable ring 78.

Figure 5:
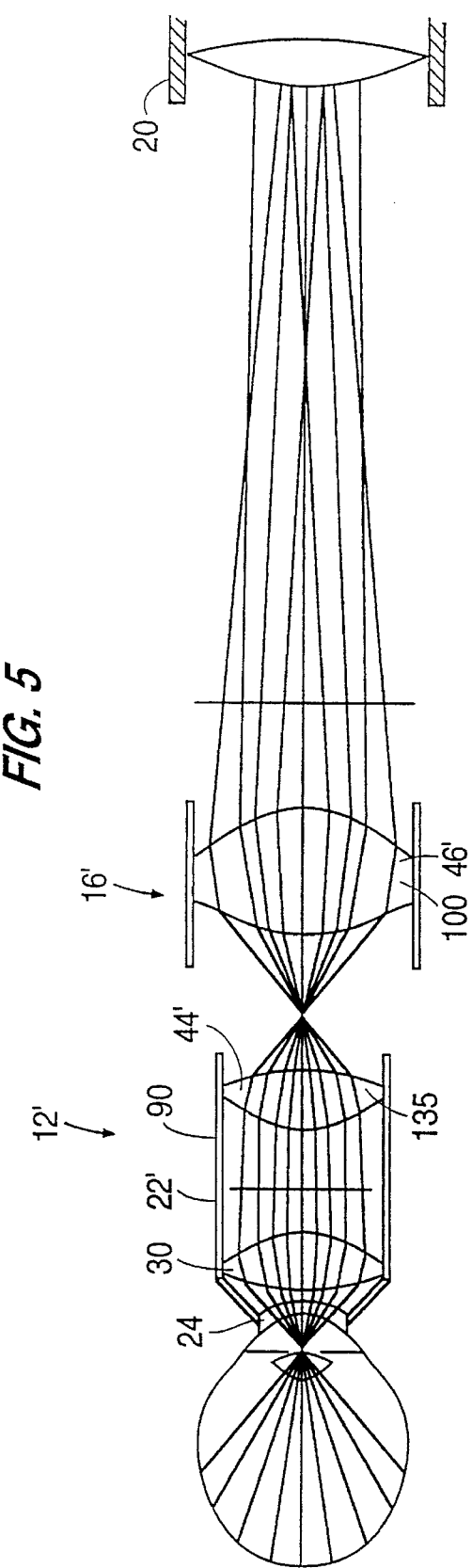
FIG. 5 is a schematic section illustrating another embodiment of the invention in which a lens component of the image erecting lens system is fixed in the holder of the contact lens device.

FIG. 5 illustrates another embodiment of the invention wherein a first lens component 44' of the image erecting lens system is mounted in a contact lens holder 22' which has an extension 90 within which lens 44' can be mounted. In this case, the separate image erecting component 16' contains a single lens system which may, in fact, comprise a single lens 46', and can either be detached from both contact lens device 12' and microscope 20 as in FIG. 1, or can be fixed to microscope 20 in a manner similar to the embodiments of FIGS. 2 to 4. In the embodiment of FIG. 5, lens 44' may be made of LAL59 glass having an index of refraction of 1,734 and have an apical posterior radius of 6,524 mm with a conic constant of −3.0, an apical anterior radius of 19.57 mm with a conic constant of −3.0 and a thickness of 5.7 mm. With this lens prescription, lens 44' may be spaced from image forming lens 30 by 9 mm so that the total length of the contact lens device 12' in FIG. 5 from the posterior surface of the contact lens element 24 to the anterior surface of lens 44' is only 22.5 mm, which is well within the range for the acceptable length of the contact lens device as previously discussed. Lens 46' may be made of SK16 glass and have an apical posterior radius of 14.66 mm with a conic constant of −2.7, an apical anterior radius 9.165 mm with a conic constant of −2.7, and a thickness of 12 mm. In general, lenses 44' and 46' are each high powered lenses within the range of 70 to 200 Diopters.

Figure 6:
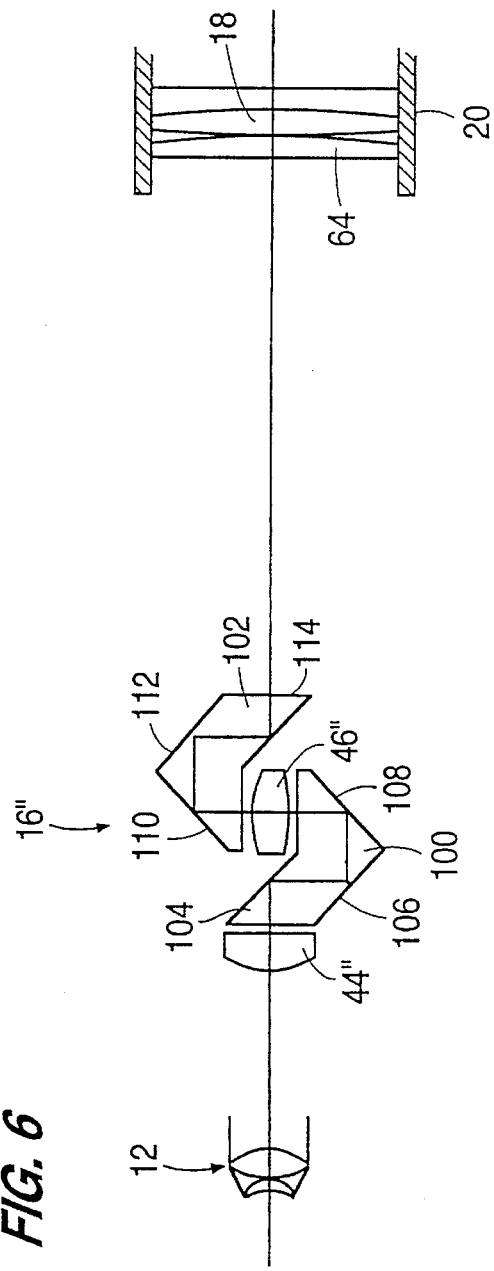
FIG. 6 is a schematic section of yet another embodiment of the invention utilizing light reflectors to fold the light passing through the second image forming lens system to minimize the working distance of the microscope.

FIG. 6 shows an embodiment of the invention which permits the use of lower powered lenses in the image erecting component which is desirable for reducing aberrations and improving image quality. However, the use of lower powered lenses 44" and 46" for example on the order of 30 Diopters, significantly increases the optical length of the system, producing an erect aerial image of the retina which is optically further removed away from the patient's eye as compared with the foregoing embodiments utilizing higher powered lenses in the image erecting lens system. The lower powered lenses would normally push back the microscope by a corresponding amount, thus increasing the working distance between the patient's eye and the end of the microscope. However, the physical distance between the patient's eye and the microscope may be minimized by the embodiment of FIG. 6 wherein reflecting surfaces provided by prisms 100 and 102 fold the path of the light rays in the manner of an accordion so that the light rays still traverse the required optical path while reducing the physical distance between the microscope 20 and the patient's eye. Alternatively, a telephoto lens system may be utilized within the erector component to accomplish a reduced length. The microscope may be brought yet closer with the use of a positively powered lens 64 as previously discussed which has the effect of shortening the focal length of the microscope.

As shown in FIG. 6, the light exiting contact lens device 12 passes through the first lens 44" of the image erecting component 16" and is reflected by 90° off of a first reflecting surface 104 of prism 100, reflected again by 90° off a second reflecting surface 106 and again 90° off a third reflecting surface 108, whereupon the light passes through the second lens 46" which is oriented at 90° relative to the first lens 44". The light then is reflected by 90° at each of reflecting surfaces 110, 112 and 114 of prism 102, whereupon the light is directed toward microscope 20. Image erecting component 16" in FIG. 6 may, like the image erecting component 16" in FIG. 5, be detached from both contact lens device 12 and microscope 20 and thus manually placed in position by the user of the microscope 20 or may be placed in position by a lens positioning device such as disclosed in my prior U.S. Pat. No. 4,934,809, or connected to the microscope in the manner described in connection with FIGS. 2–4.

As may be appreciated from the foregoing, the idea of the invention is to take advantage of the large field of view afforded by an indirect contact ophthalmoscopy lens device and to reinvert the inverted aerial image produced by the contact lens device with the use of an image erecting component that is separate from the contact lens device. The use of such a separate image erecting component allows the length of the contact lens device to be maintained within an acceptable range that will minimize discomfort of the patient and add to the convenience of the physician performing a surgical procedure or simply observing the patient's retina through the microscope. With the use of a separate image erecting component according to the invention, the physician, by adjusting the position of the image erecting component, is able to scan and optimize the view of the inverted image produced by the contact lens device while maintaining the position of the contact lens device and the microscope fixed. In the case where the separate image erecting component is mounted independently of both the contact lens element and the microscope, the microscope may be moved without diminution or loss of the real inverted image produced by the contact lens device.

The invention has been described in detail with respect to preferred embodiments, and it will now be apparent from the foregoing to those skilled in the art that changes and modifications may be made without departing from the invention in its broader aspects, and the invention, therefore, as defined in the appended claims is intended to cover all such changes and modifications as fall within the true spirit of the invention.

What is claimed is:

1. An indirect ophthalmoscopy lens system, comprising:
   a contact lens device including a first holder, a contact lens element having a concave posterior surface for placement on a cornea of a patient's eye and a first image forming lens system located anterior of the contact lens element and cooperating with the contact lens element for focussing light emanating from the retina of the patient's eye for forming a real, inverted, aerial image of the patient's retina anterior of the first image forming lens system, the first holder mounting the contact lens element and the first image forming lens system in a fixed relationship to one another; and
   an image erecting component including a second holder detached from the first holder and a second image forming lens system mounted within said second holder for receiving light rays forming the real inverted image anterior of the first image forming lens system for forming a real, re-inverted, aerial image of the patient's retina anterior of the second image forming lens system.

2. An indirect ophthalmoscopy lens system according to claim 1, and further comprising mounting means coupled to the second holder for mounting the image erecting component separate from and anterior to the contact lens device.

3. An indirect ophthalmoscopy lens system according to claim 2, wherein said mounting means includes means for mounting the image erecting component to a microscope through which the real, re-inverted, aerial image of the patient's retina produced by said image erecting component can be observed.

4. An indirect ophthalmoscopy lens system according to claim 3, wherein said mounting means mounts the image erecting component to the microscope so that the second image forming lens system has a fixed coaxial relationship with the microscope.

5. An indirect ophthalmoscopy lens system according to claim 3, wherein said mounting means includes means for adjustably rotating the image erecting component about an optical axis of the microscope.

6. An indirect ophthalmoscopy lens system according to claim 3, wherein said mounting means includes means for adjustably moving the image erecting component in a plane transverse to an optical axis of the microscope.

7. An indirect ophthalmoscopy lens system according to claim 3, wherein said mounting means includes means for adjustably moving the image erecting component in a direction extending between the contact lens device and the microscope.

8. An indirect ophthalmoscopy lens system according to claim 3, wherein said mounting means includes a universal joint coupled to said second holder for universally pivoting the image erecting component.

9. An indirect ophthalmoscopy lens system according to claim 1, wherein said second image forming lens system comprises first and second lens systems spaced from one another for forming the real, re-inverted, aerial image of the patient's retina anterior of the second lens system.

10. An indirect ophthalmoscopy lens system according to claim 9, wherein a microscope is used to view the erect aerial image produced by the image erecting component, and said second image forming lens system further comprises optical means for minimizing a working distance from the microscope.

11. An indirect ophthalmoscopy lens system according to claim 10, wherein said minimizing means comprises light folding means which are operatively arranged with the first and second lens systems for folding the light rays emanating from the first lens system to minimize a physical distance to the microscope while maintaining required optical distances to the microscope and within the second image forming lens system.

12. An indirect ophthalmoscopy lens system according to claim 11, wherein said light folding means comprises at least one of a prism system and a mirror system arranged for achieving the folding of the light rays.

13. An indirect ophthalmoscopy lens system according to claim 2, wherein a microscope is used to view the erect aerial image produced by the image erecting component, and further comprising a further lens system having positive optical power and mounted anterior of the second image forming lens system, wherein the real, re-inverted, aerial image is formed between the further lens system and the second image forming lens system and the further lens system has the effect of reducing a focal length of the microscope.

14. An indirect ophthalmoscopy lens system according to claim 2, further including mounting means for mounting the image erecting component to a microscope through which the real, re-inverted, aerial image produced by said image erecting component can be observed, said image erecting component further comprising a further lens system having positive optical power and mounted anterior of the second image forming lens system, wherein the real, re-inverted, aerial image is formed between the further lens systems and the second image forming lens system and the further lens system has the effect of reducing a focal length of the microscope.

15. An indirect ophthalmoscopy lens system according to claim 2, wherein said contact lens device has an optical axis and said mounting means includes means for adjustably moving the image erecting component in a direction transverse to the optical axis of the contact lens device when said contact lens device is positioned on the eye of a patient.

16. An indirect ophthalmoscopy lens system according to claim 2, wherein said contact lens device has an optical axis and said mounting means includes means for adjustably moving said image erecting component in a direction of the optical axis of the contact lens device when the contact lens device is positioned on the eye of a patient.

17. An indirect ophthalmoscopy lens system according to claim 2, wherein said mounting means includes a universal joint coupled to said second holder for universally pivoting the image erecting component.

\* \* \* \* \*